(12) United States Patent
Akita et al.

(10) Patent No.: US 10,652,973 B2
(45) Date of Patent: May 12, 2020

(54) CONTROL APPARATUS, CONTROL SYSTEM, AND CONTROL METHOD

(71) Applicant: SONY CORPORATION, Tokyo (JP)

(72) Inventors: Masayoshi Akita, Tokyo (JP); Tsuneo Hayashi, Tokyo (JP); Yuki Sugie, Kanagawa (JP); Akio Furukawa, Tokyo (JP); Mitsunori Ueda, Tokyo (JP); Hiroshi Ichiki, Kanagawa (JP); Daisuke Kikuchi, Kanagawa (JP)

(73) Assignee: SONY CORPORATION, Tokyo (JP)

( * ) Notice: Subject to any disclaimer, the term of this patent is extended or adjusted under 35 U.S.C. 154(b) by 0 days.

(21) Appl. No.: 16/308,613

(22) PCT Filed: Apr. 24, 2017

(86) PCT No.: PCT/JP2017/016205
§ 371 (c)(1),
(2) Date: Dec. 10, 2018

(87) PCT Pub. No.: WO2018/025457
PCT Pub. Date: Feb. 8, 2018

(65) Prior Publication Data
US 2019/0261498 A1 Aug. 22, 2019

(30) Foreign Application Priority Data
Aug. 1, 2016 (JP) .................................. 2016-151394

(51) Int. Cl.
*H05B 33/00* (2006.01)
*H05B 37/02* (2006.01)
(Continued)

(52) U.S. Cl.
CPC ..... *H05B 37/0281* (2013.01); *A61B 1/00006* (2013.01); *A61B 1/00009* (2013.01);
(Continued)

(58) Field of Classification Search
CPC ............ H05B 33/0857; H05B 33/0803; H05B 37/0254; H05B 33/0818; H05B 33/0827;
(Continued)

(56) References Cited

U.S. PATENT DOCUMENTS

| 2008/0232086 | A1 | 9/2008 | Marka et al. |
| 2017/0143442 | A1* | 5/2017 | Tesar ................. A61B 90/37 |

(Continued)

FOREIGN PATENT DOCUMENTS

| JP | 2009-515618 A | 4/2009 |
| JP | 2012-245349 A | 12/2012 |

(Continued)

OTHER PUBLICATIONS

International Search Report dated Jul. 25, 2017 in PCT/JP2017/016205 filed on Apr. 24, 2017.

*Primary Examiner* — Monica C King
(74) *Attorney, Agent, or Firm* — Xsensus LLP

(57) ABSTRACT

[Object] To propose a control apparatus, a control system and a control method which are capable of causing another light source to adaptively emit light at a timing at which light emitted from one light source changes.
[Solution] A control apparatus including: a light source control unit configured to control light emission of a second light source on the basis of profile of light emitted from a first light source and a synchronization signal for synchronizing a timing between the first light source and the second light source for radiating light on a surgical region.

20 Claims, 14 Drawing Sheets

(51) Int. Cl.
  *A61B 90/30* (2016.01)
  *H05B 39/04* (2006.01)
  *A61B 1/06* (2006.01)
  *A61B 1/00* (2006.01)
  *A61B 1/045* (2006.01)

(52) U.S. Cl.
  CPC .......... *A61B 1/00039* (2013.01); *A61B 1/045* (2013.01); *A61B 1/0638* (2013.01); *A61B 90/30* (2016.02); *H05B 37/02* (2013.01); *H05B 39/044* (2013.01); *Y02B 20/42* (2013.01)

(58) Field of Classification Search
  CPC .. H05B 37/029; H05B 33/0863; H05B 37/02; H05B 33/0842; H05B 33/0869; H05B 33/0872; H05B 33/0815; H05B 33/0896
  See application file for complete search history.

(56) References Cited

U.S. PATENT DOCUMENTS

2018/0368656 A1* 12/2018 Austin ................. A61B 1/0005
2019/0187641 A1*  6/2019 Tsubota ................ G05B 19/00

FOREIGN PATENT DOCUMENTS

| JP | 2014-220169 A | 11/2014 |
| JP | 2015-169438 A |  9/2015 |

\* cited by examiner

FIG. 6
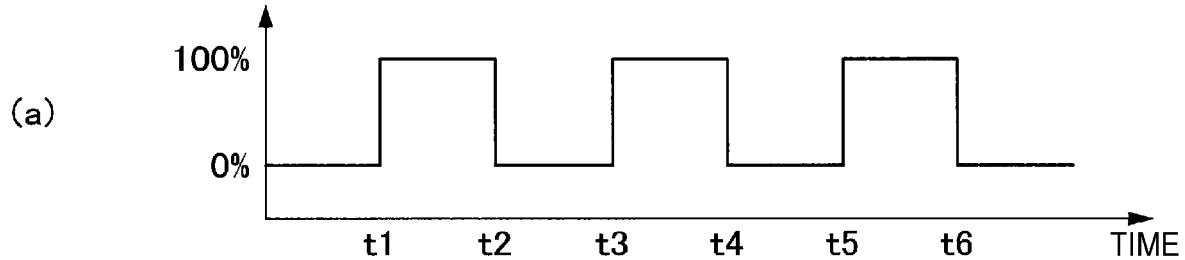
(a) LIGHT EMISSION INTENSITY OF EXTERNAL LIGHT SOURCE
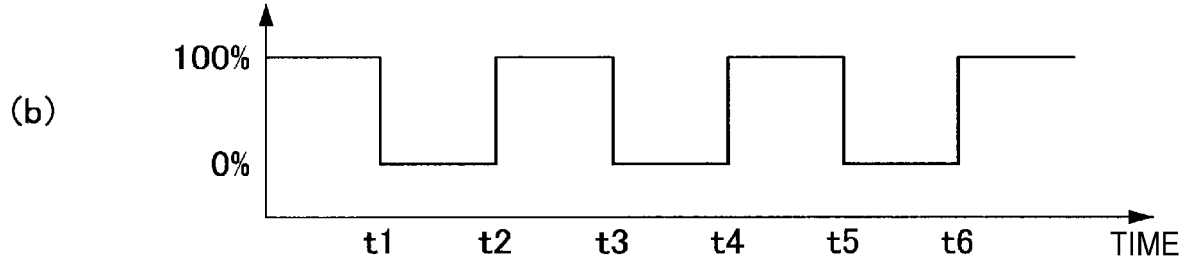
(b) LIGHT EMISSION INTENSITY OF OWN LIGHT SOURCE
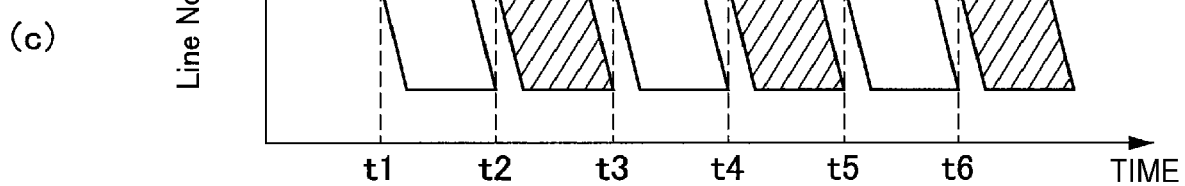
(c)

FIG. 11
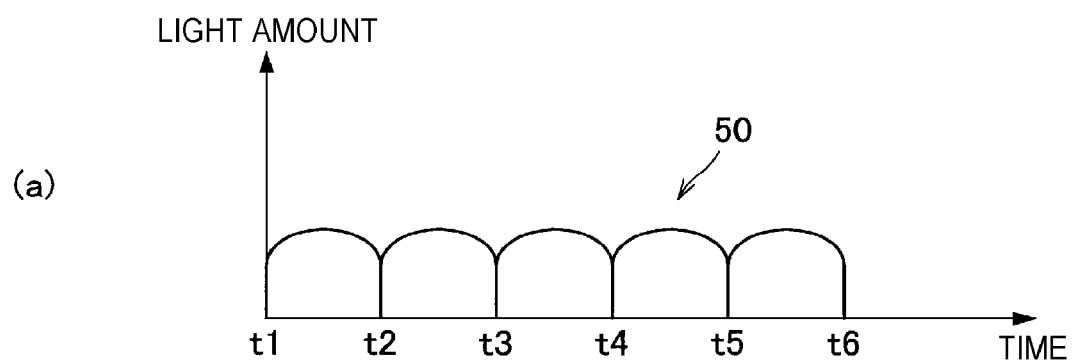
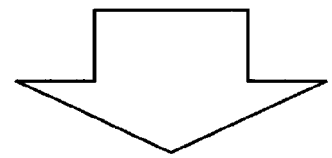
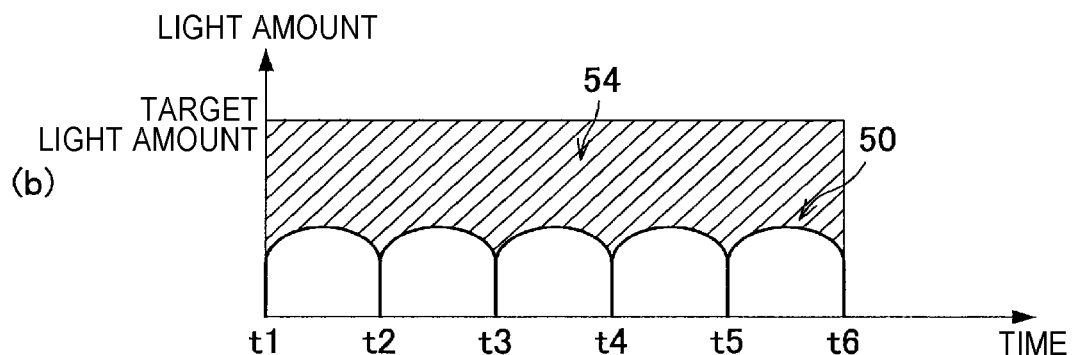

FIG. 12
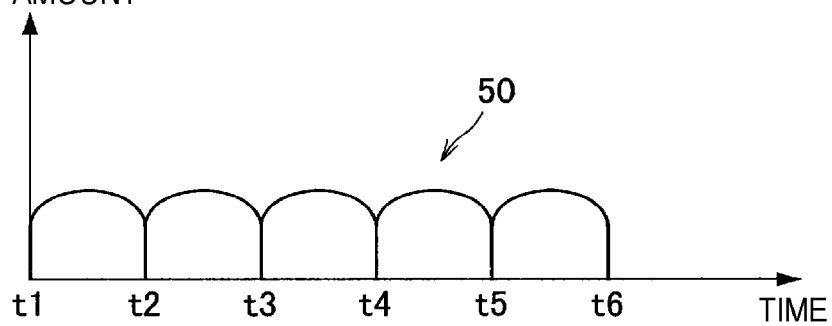
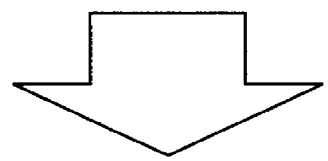
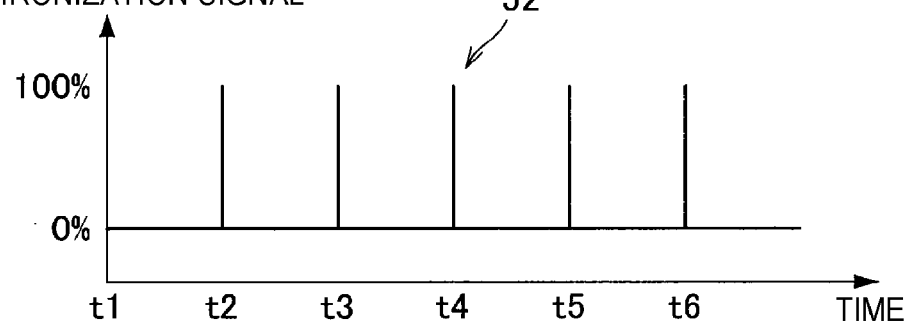

CONTROL APPARATUS, CONTROL SYSTEM, AND CONTROL METHOD

TECHNICAL FIELD

The present disclosure relates to a control apparatus, a control system, and a control method.

BACKGROUND ART

In related art, various kinds of lighting equipment such as, for example, a light emitting diode (LED) and fluorescent lighting have been developed.

Further, various kinds of technologies for acquiring data from a measurement target using a measuring apparatus such as, for example, a microscope apparatus have been proposed (see, for example, the following Patent Literature 1).

CITATION LIST

Patent Literature

Patent Literature 1: JP 2015-169438A

DISCLOSURE OF INVENTION

Technical Problem

By the way, brightness of light emitted from one light source can change over time. Therefore, for example, in a scene in which imaging is performed while light is emitted by one light source, brightness of a picked up image changes in accordance with an imaging timing.

Therefore, the present disclosure proposes a new and improved control apparatus, control system and control method which are capable of causing another light source to adaptively emit light at a timing at which light emitted from one light source changes.

Solution to Problem

According to the present disclosure, there is provided a control apparatus including: a light source control unit configured to control light emission of a second light source on the basis of profile of light emitted from a first light source and a synchronization signal for synchronizing a timing between the first light source and the second light source for radiating light on a surgical region.

In addition, according to the present disclosure, there is provided a control system including: a first light source; a second light source configured to radiate light on a surgical region; an image pickup unit; a light source control unit configured to control light emission of the second light source on the basis of profile of light emitted from the first light source, and a synchronization signal for synchronizing a timing between the first light source and the second light source; and an imaging control unit configured to control imaging of the image pickup unit on the basis of the synchronization signal.

In addition, according to the present disclosure, there is provided a control method including: controlling, by a processor, light emission of a second light source on the basis of profile of light emitted from a first light source and a synchronization signal for synchronizing a timing between the first light source and the second light source for radiating light on a surgical region.

Advantageous Effects of Invention

As described above, according to the present disclosure, it is possible to cause another light source to adaptively emit light at a timing at which light emitted from one light source changes. Note that effects described here are not necessarily limitative, and may be any effect disclosed in the present disclosure.

BRIEF DESCRIPTION OF DRAWINGS

FIG. 6 is an explanatory diagram illustrating an example of light emission control on a light source unit 202 and imaging control according to the first embodiment.

FIG. 11 is an explanatory diagram illustrating a generation example of own light source profile according to the second embodiment.

FIG. 12 is an explanatory diagram illustrating a detection example of a synchronization signal according to the second embodiment.

MODE(S) FOR CARRYING OUT THE INVENTION

Figure 1:
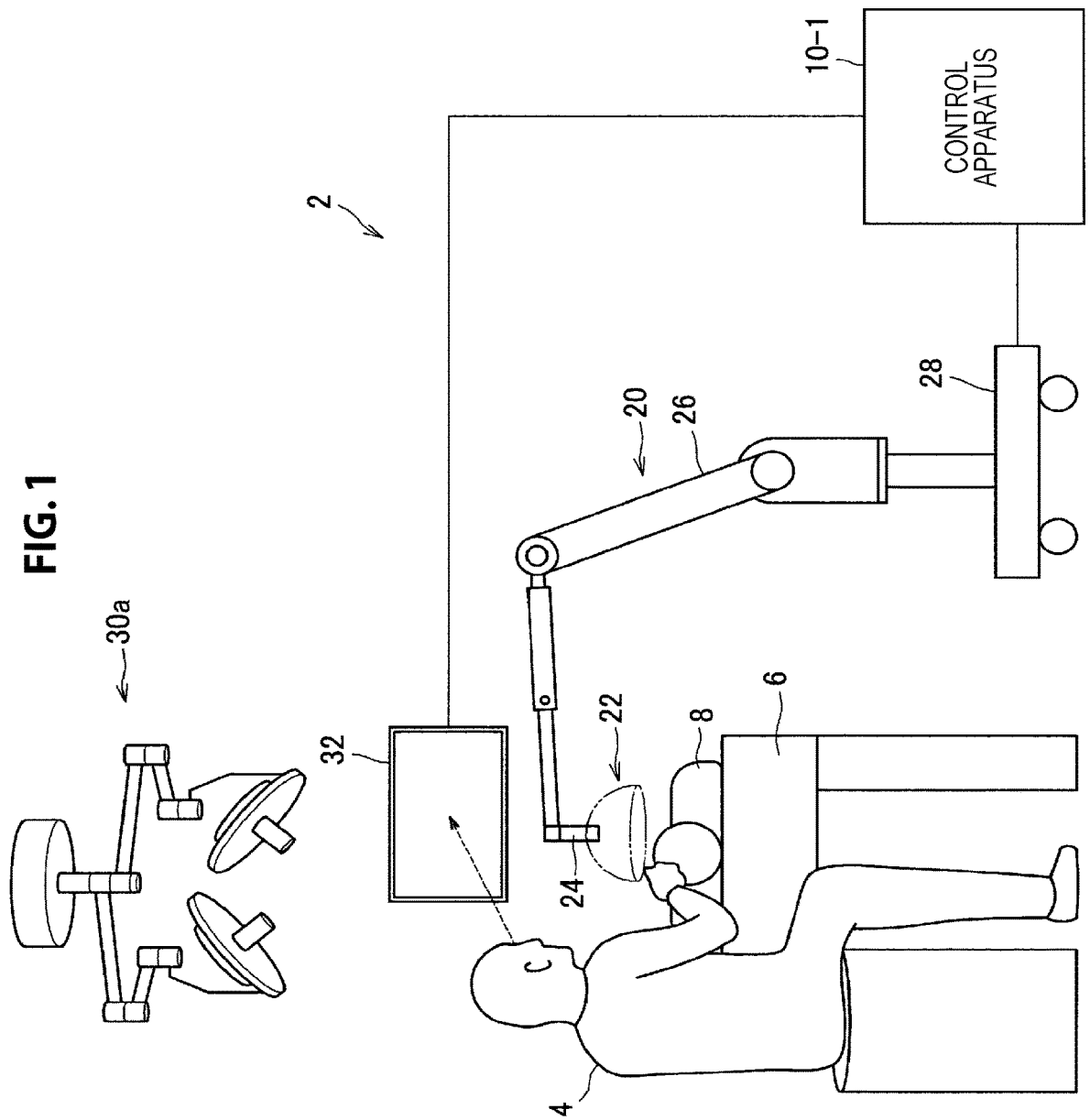
FIG. 1 is an explanatory diagram illustrating a configuration example of a control system according to a first embodiment.

Hereinafter, a preferred embodiment of the present disclosure will be described in detail with reference to the appended drawings. Note that, in this specification and the appended drawings, structural elements that have substantially the same function and structure are denoted with the same reference numerals, and repeated explanation of these structural elements is omitted.

Further, in the present specification and drawings, there is a case where a plurality of components having substantially the same functional configuration are distinguished by different alphabetical characters being assigned after the same reference numeral. For example, a plurality of components having substantially the same functional configuration are distinguished as necessary as a control apparatus 10-1a and a control apparatus 10-1b. However, in the case where it is not necessary to particularly distinguish among a plurality of components having substantially the same functional configuration, only the same reference numeral is assigned. For example, in the case where it is not necessary to particularly distinguish between the control apparatus 10-1a and the control apparatus 10-1b, they are simply referred to as a control apparatus 10-1.

Further, the "Mode(s) for Carrying Out the Invention" will be described in accordance with the following item order.
1. First Embodiment
2. Second Embodiment
3. Third Embodiment
4. Modified examples Note that, in the present specification and the drawings, there is a case where a control apparatus 10-1, a control apparatus 10-2 and a control apparatus 10-3 according to each embodiment which will be described later are collectively referred to as a control apparatus 10.

1. First Embodiment

<1-1. Configuration of Control System>

First, a first embodiment will be described. In the first embodiment, a scene will be mainly described in which a medical doctor performs craniotomy procedure while utilizing an observation apparatus 20 which will be described later in a surgery room. Note that the first embodiment can be applied to a scene in which open procedure such as laparotomy procedure and thoracotomy procedure is performed, as well as a scene of craniotomy procedure.

FIG. 1 is an explanatory diagram illustrating a configuration example of a control system according to the first embodiment. As illustrated in FIG. 1, the control system according to the first embodiment includes an observation system 2 and an external light source 30. Further, the observation system 2 includes a control apparatus 10-1, the observation apparatus 20 and a display apparatus 32. Note that FIG. 1 illustrates a state where a surgeon 4 is using the control system to perform surgery for a patient 8 on a patient bed 6. Further, in the following description concerning the control system, a "user" means an arbitrary one of medical staff members such as a surgeon or an assistant who uses the control system.

{1-1-1. Observation Apparatus 20}

The observation apparatus 20 includes an observing unit 22 for observing an observation target (surgical region of a patient), an arm unit 26 which supports the observing unit 22 at a distal end thereof, and a base unit 28 which supports a proximal end of the arm unit 26.

The observing unit 22 includes a cylindrical portion 24 having a substantially cylindrical shape, an image pickup unit 200 (not illustrated in FIG. 1) provided inside the cylindrical portion 24, and an operation unit (not illustrated) provided in a partial region of an outer circumference of the cylindrical portion 24.

The observing unit 22 is, for example, a microscope unit. As an example, the observing unit 22 is a microscope unit of the electronic image pickup type (so-called microscope unit of the video type) which electronically picks up an image by the image pickup unit 200.

A cover glass member for protecting the internal image pickup unit 200 is provided at an opening face of a lower end of the cylindrical portion 24. Light from an observation target (hereinafter, also referred to as observation light) passes through the cover glass member and enters the image pickup unit 200 inside the cylindrical portion 24. Further, a light source unit 202 is provided inside the cylindrical portion 24. Then, upon imaging, light may be radiated upon the observation target from the light source unit 202 through the cover glass member.

The light source unit 202 is an example of a second light source in the present disclosure. The light source unit 202 can be, for example, an LED and a semiconductor light source such as a semiconductor laser. The light source unit 202 can adjust a radiation light amount of the light source unit 202, a wavelength (color) of irradiation light, an irradiation direction of light, or the like, as appropriate. For example, the light source unit 202 can radiate visible light and infrared light.

The image pickup unit 200 includes an optical system which condenses observation light, and an image pickup element which receives the observation light condensed by the optical system. The optical system includes a combination of a plurality of lenses including a zoom lens and a focusing lens. The optical system has optical properties adjusted such that the observation light is condensed to be formed image on a light receiving face of the image pickup element. The image pickup element receives and photoelectrically converts the observation light to generate a signal corresponding to the observation light, namely, an image signal corresponding to an observation image. As the image pickup element, for example, an image pickup element which has a Bayer array and is capable of picking up an image in color is used. The image pickup element may be any of various known image pickup elements such as a complementary metal oxide semiconductor (CMOS) image sensor or a charge coupled device (CCD) image sensor. The image signal generated by the image pickup element is transmitted as RAW data to the control apparatus 10-1 described later. Here, the transmission of the image signal may be performed suitably by optical communication. This is because, since, at a surgery site, the surgeon performs surgery while observing the state of an affected area through a picked up image, in order to achieve surgery with a higher degree of safety and certainty, it is demanded for a moving image of the surgical region to be displayed on the real time basis as far as possible. Where optical communication is used to transmit the image signal, the picked up image can be displayed with low latency.

It is to be noted that the image pickup unit 200 may have a driving mechanism for moving the zoom lens and the focusing lens of the optical system thereof along the optical axis. Where the zoom lens and the focusing lens are moved suitably by the driving mechanism, the magnification of the picked up image and the focal distance upon image picking up can be adjusted. Further, the image pickup unit 200 may incorporate therein various functions which may be provided generally in a microscopic unit of the electronic image pickup such as an auto exposure (AE) function or an auto focus (AF) function.

Further the image pickup unit 200 may be configured as an image pickup unit 200 of the single-plate type which includes a single image pickup element or may be configured as an image pickup unit 200 of the multi-plate type which includes a plurality of image pickup elements. Where the image pickup unit 200 is configured as that of the multi-plate type, for example, image signals corresponding to red, green, and blue colors may be generated by the image pickup elements and may be synthesized to obtain a color image. Alternatively, the image pickup unit 200 may be configured such that it has a pair of image pickup elements for acquiring image signals for the right eye and the left eye compatible with a stereoscopic vision (three dimensional (3D) display). Where 3D display is applied, the surgeon can comprehend the depth of a living body tissue in the surgical region with a higher degree of accuracy. It is to be noted that, if the image pickup unit 200 is configured as that of stereoscopic type, then a plurality of optical systems are provided corresponding to the individual image pickup elements.

The operation unit includes, for example, a cross lever, a switch or the like and accepts an operation input of the user. For example, the user can input an instruction to change the magnification of the observation image and the focal distance to the observation target through the operation unit. The magnification and the focal distance can be adjusted by the driving mechanism of the image pickup unit 200 suitably moving the zoom lens and the focusing lens in accordance with the instruction. Further, for example, the user can input an instruction to switch the operation mode of the arm unit 26 (an all-free mode and a fixed mode hereinafter described) through the operation unit. It is to be noted that when the user intends to move the observing unit 22, it is supposed that the user moves the observing unit 22 in a state in which the user grasps the observing unit 22 holding the cylindrical portion 24. Accordingly, the operation unit is preferably provided at a position at which it can be operated readily by the fingers of the user with the cylindrical portion 24 held such that the operation unit can be operated even while the user is moving the cylindrical portion 24.

The arm unit 26 is configured such that a plurality of links are connected for rotation relative to each other by a plurality of joint portions.

{1-1-2. Control Apparatus 10-1}

The control apparatus 10-1 integrally controls operation of the observation system 2 by controlling operation of the observation apparatus 20 and the display apparatus 32. For example, the control apparatus 10-1 renders the actuators of the respective joint portions within the arm unit 26 operative in accordance with a predetermined control method to controls driving of the arm unit 26. Further, for example, the control apparatus 10-1 performs various signal processes for an image signal acquired by the image pickup unit 200 of the observation apparatus 20 to generate image data for display and controls the display apparatus 32 to display the generated image data. As the signal processes, various known signal processes such as, for example, a development process (demosaic process), an image quality improving process (a bandwidth enhancement process, a super-resolution process, a noise reduction (NR) process and/or an image stabilization process) and/or an enlargement process (namely, an electronic zooming process) may be performed.

Note that communication between the control apparatus 10-1 and the observing unit 22 and communication between the control apparatus 10-1 and the respective joint portions within the arm unit 26 may be wired communication or wireless communication. Where wired communication is applied, communication by an electric signal may be performed or optical communication may be performed. In this case, a cable for transmission used for wired communication may be configured as an electric signal cable, an optical fiber or a composite cable of them in response to an applied communication method. On the other hand, where wireless communication is applied, since there is no necessity to lay a transmission cable in the surgery room, such a situation that movement of medical staff in the surgery room is disturbed by a transmission cable can be eliminated.

The control apparatus 10-1 may include a processor such as a central processing unit (CPU) or a graphics processing unit (GPU), or a microcomputer or a control board in which a processor and a storage element such as a memory are incorporated. The various functions described hereinabove can be implemented by the processor of the control apparatus 10-1 operating in accordance with a predetermined program. The control apparatus 10-1 can also include a programmable logic device such as a field-programmable gate array (FPGA) in place of the processor or along with the processor. In this case, by the FPGA of the control apparatus 10-1 operating in accordance with a configuration designated by a user using hardware description language, or the like, the above-described various kinds of functions can be implemented.

Note that, while, in the illustrated drawing, the control apparatus 10-1 is provided as an apparatus separate from the observation apparatus 20, the control apparatus 10-1 may be provided inside the base unit 28 of the observation apparatus 20 or may be configured integrally with the observation apparatus 20. The control apparatus 10-1 may also include a plurality of apparatuses. For example, microcomputers, control boards, or the like, may be disposed at the observing unit 22 or the respective joint portions within the arm unit 26 and connected for communication with each other to implement functions similar to those of the control apparatus 10-1.

{1-1-3. Display Apparatus 32}

The display apparatus 32 is provided in the surgery room and displays an image corresponding to image data generated by the control apparatus 10-1 under the control of the control apparatus 10-1. In other words, an image of a surgical region picked up by the observing unit 22 is displayed on the display apparatus 32. The display apparatus 32 may display, in place of or in addition to an image of a surgical region, various kinds of information relating to the surgery such as physical information of a patient or information regarding a surgical procedure of the surgery. In this case, the display of the display apparatus 32 may be switched suitably in response to an operation by the user. Alternatively, a plurality of such display apparatus 32 may also be provided such that an image of a surgical region or various kinds of information relating to the surgery may individually be displayed on the plurality of display apparatus 32. It is to be noted that, as the display apparatus 32, various known display apparatus such as a liquid crystal display apparatus or an electro luminescence (EL) display apparatus may be applied.

For example, as depicted in FIG. 1, upon surgery, an image of a surgical region picked up by the observation apparatus 20 is, for example, displayed in an enlarged scale on the display apparatus 32 installed on a wall face of the surgery room. The display apparatus 32 is installed at a position opposing to the surgeon 4, and the surgeon 4 would perform various treatments for the surgical region such as, for example, resection of the affected area while observing a state of the surgical region from a video displayed on the display apparatus 32.

Note that the display apparatus 32 may be provided by being hung from a ceiling of the surgery room or may be placed on a disk within the surgery room, as well as an example where the display apparatus 32 is installed on a wall face of the surgery room. Alternatively, the display apparatus 32 may be mobile equipment having a display function or may be configured integrally with the control apparatus 10-1 or the observation apparatus 20.

{1-1-4. External Light Source 30}

The external light source 30 is an example of a first light source in the present disclosure. The external light source 30 is a light source provided within the surgery room. For example, the external light source 30 is provided on a ceiling of the surgery room and irradiates at least hands of the surgeon. The external light source 30 may be able to adjust an irradiation light amount of the external light source 30, a wavelength (color) of irradiation light, an irradiation direction of light, or the like, as appropriate. At this external light source 30, brightness of emitted light can periodically change, which includes blinking in accordance with a commercial power supply frequency (for example, equal to or higher than 50 Hz).

This external light source 30 can be a shadowless lamp. Further, the external light source 30 can include an LED.

Note that the configuration of the control system according to the first embodiment is not limited to the above-described example. For example, the observation apparatus 20 can also function as a supporting arm apparatus which supports, at a distal end thereof, other observation apparatuses such as, for example, an endoscope in place of the observing unit 22. That is, the control system (or the observation system 2) can be applied to a microscopic surgery system and an endoscopic surgery system. Here, other observation apparatuses include the image pickup unit 200. Further, other observation apparatuses may further include the light source unit 202 or do not have to include the light source unit 202. In the latter case, the light source unit 202 can be supported by the supporting arm apparatus separately from other observation apparatuses. By these observation apparatuses (and the light source unit 202) being supported by the supporting arm apparatus, it becomes possible to fix a position more stably and reduce burden on medical staff compared to a case where these observation apparatuses are supported by hands of the medical staff {1-1-5. Organization of Problems}

The configuration of the control system according to the first embodiment has been described above. By the way, in related art, infrared excitation fluorescent observation using indocyanine green (ICG), that is, observation of a fluorescent image by local injection of ICG into tissue and irradiation on the tissue with excitation light corresponding to a fluorescent wavelength of a reagent is performed. However, upon open procedure, it is necessary to darken inside the surgery room to perform infrared excitation fluorescent observation using ICG.

Further, as another problem, because the external light source 30 is not in synchronization with the observation system 2, artifact such as banding which is a phenomenon that a bright portion and a dark portion appear, and flicker can occur within an image picked up by the image pickup unit 200.

Therefore, in view of the above-described circumstances, the control apparatus 10-1 according to the first embodiment has been created. According to the first embodiment, the control apparatus 10-1 controls light emission of the light source unit 202 on the basis of profile of light emitted from the external light source 30 (hereinafter, referred to as external light source profile) and a synchronization signal specified on the basis of the light emitted from the external light source 30. By this means, it is possible to cause the light source unit 202 to adaptively emit light at a timing at which brightness of the light emitted from the external light source 30 changes. For example, it is possible to cause the light source unit 202 to emit infrared light when the external light source 30 does not emit light or cause the light source unit 202 to emit visible light so as to compensate for a lack of a light amount of the external light source 30.

<1-2. Configuration>

Figure 2:
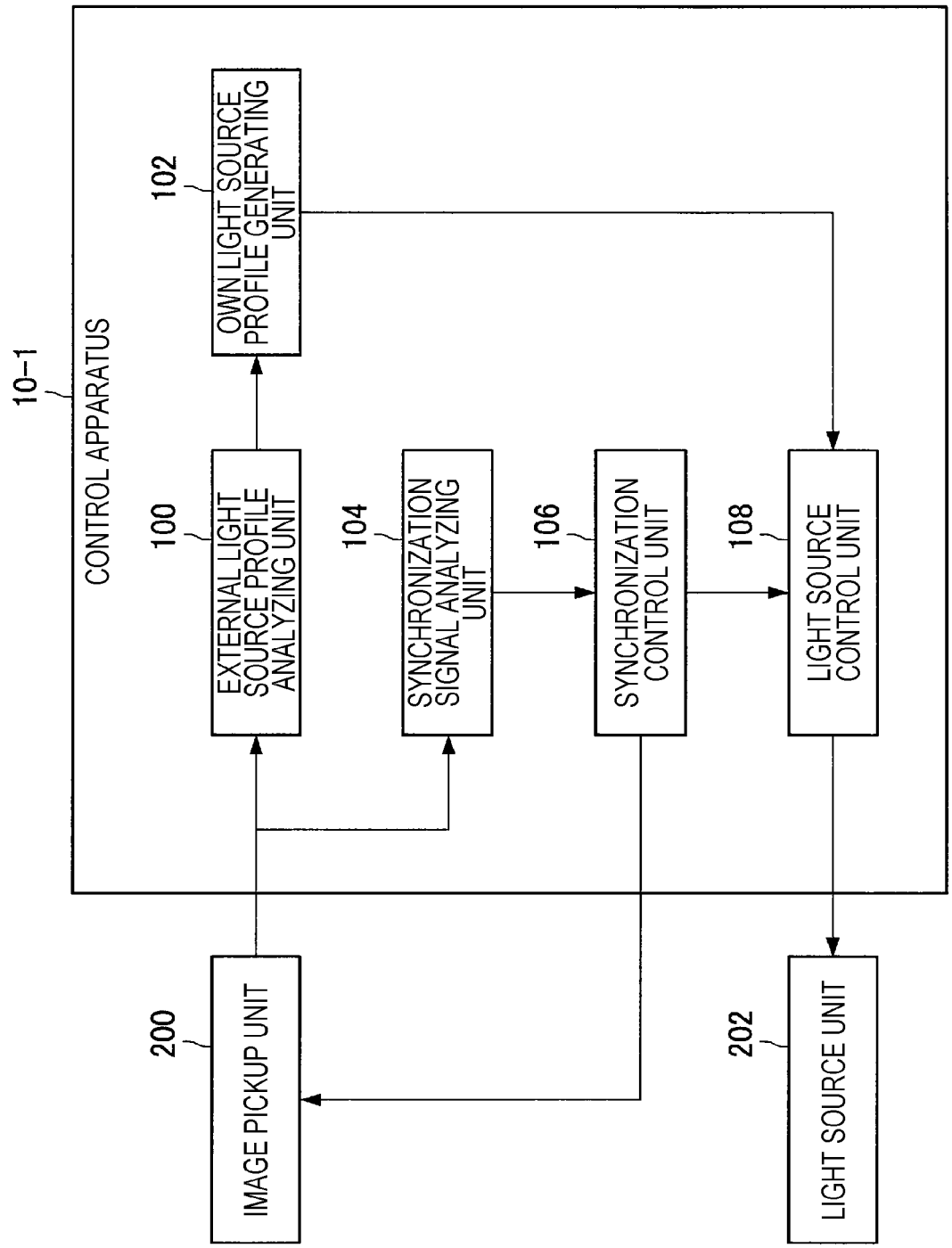
FIG. 2 is a functional block diagram illustrating a configuration example of a control apparatus 10-1 according to the first embodiment.

A configuration of the control apparatus 10-1 according to the first embodiment will be described in detail next. FIG. 2 is a functional block diagram illustrating a configuration example of the control apparatus 10-1 according to the first embodiment. As illustrated in FIG. 2, the control apparatus 10-1 includes an external light source profile analyzing unit 100, an own light source profile generating unit 102, a synchronization signal analyzing unit 104, a synchronization control unit 106 and a light source control unit 108.

{1-2-1. External Light Source Profile Analyzing Unit 100}

The external light source profile analyzing unit 100 is an example of a profile specifying unit in the present disclosure. The external light source profile analyzing unit 100 analyzes external light source profile on the basis of an image of a subject which is irradiated with light from the external light source 30, which is picked up by the image pickup unit 200. Here, the external light source profile can include information regarding regularity of change of brightness of light emitted from the external light source 30. For example, the external light source profile includes a modulation pattern, a light emission frequency and illumination color of the light emitted from the external light source 30.

For example, the external light source profile analyzing unit 100, first, specifies a length of a period during which a relatively bright image is picked up (that is, a period during which light emission intensity of the external light source 30 is relatively high) and a length of a period during which a relatively dark image is picked up (that is, a period during which light emission intensity of the external light source 30 is relatively low) on the basis of imaging by the image pickup unit 200. For example, in the case where the external light source 30 is LED lighting, the external light source profile analyzing unit 100 specifies a length of a period during which the external light source 30 is turned on and a length of a period during which the external light source 30 is turned off on the basis of imaging by the image pickup unit 200.

Figure 3:
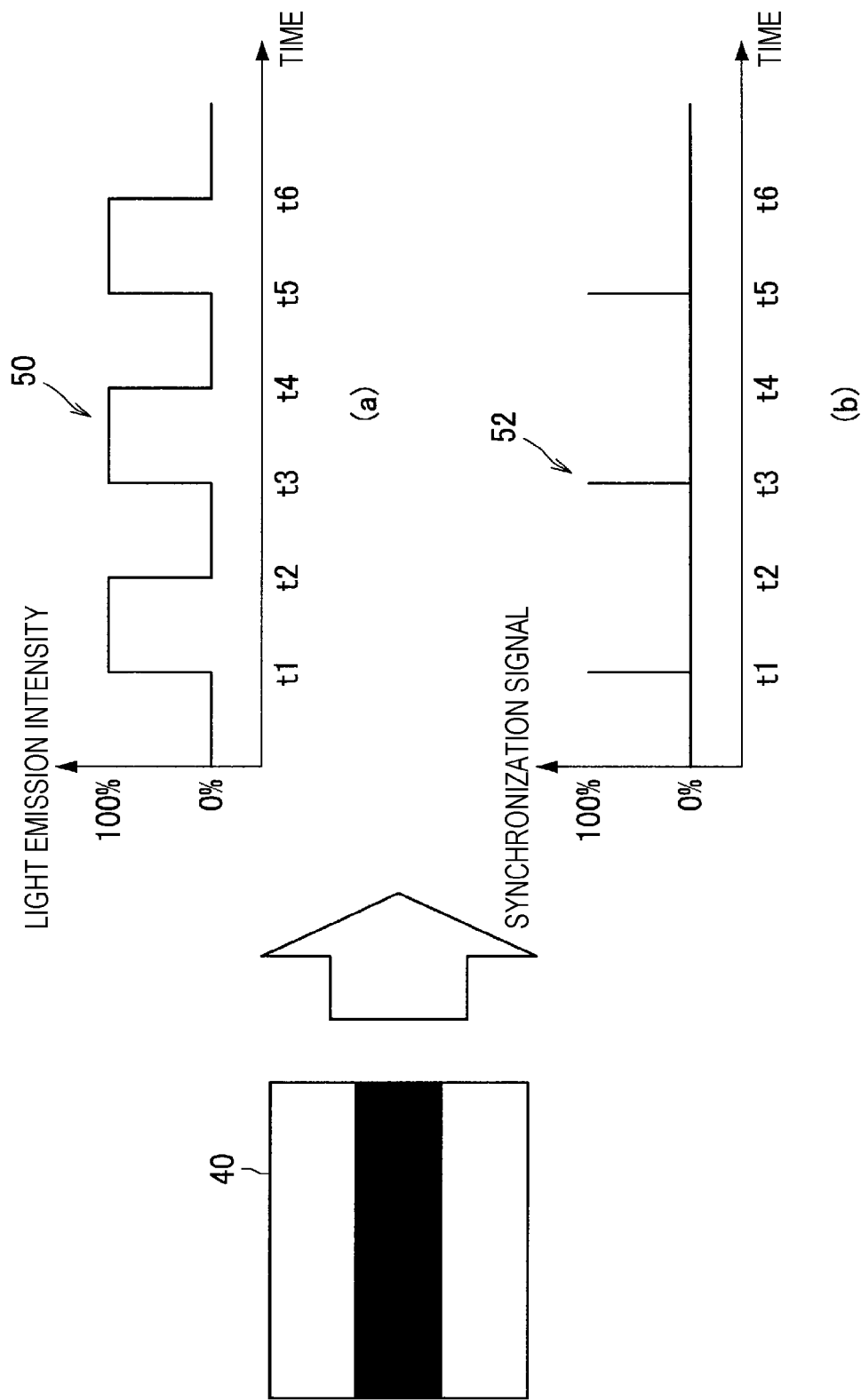
FIG. 3 is an explanatory diagram illustrating an analysis example of external light source profile and a synchronization signal according to the first embodiment.

Then, the external light source profile analyzing unit 100 analyzes a cycle of light emission of the external light source 30 on the basis of relationship between these lengths of periods. By this means, a waveform 50 of light emission intensity of the external light source 30 as illustrated in a graph (a) in FIG. 3 can be specified.

Note that the external light source profile analyzing unit 100 can also analyze the external light source profile on the basis of a still image picked up by the image pickup unit 200 or can also analyze the external light source profile on the basis of a picked up moving image, that is, a series of images. Further, the external light source profile analyzing unit 100 basically analyzes the external light source profile in real time (for example, during surgery). However, the present disclosure is not limited to such an example, and the external light source profile analyzing unit 100 may analyze the external light source profile in advance, for example, before surgery, or the like.

(1-2-1-1. Modified Example)

Note that, as a modified example, all or part of information included in the external light source profile can be preset at the control apparatus 10-1 or other apparatuses which can communicate with the control apparatus 10-1. In this case, the external light source profile analyzing unit 100 can also acquire the external light source profile by acquiring the preset information from the corresponding apparatus.

{1-2-2. Own Light Source Profile Generating Unit 102}

The own light source profile generating unit 102 generates own light source profile on the basis of the external light source profile analyzed by the external light source profile analyzing unit 100. Further, the own light source profile generating unit 102 can further generate the own light source profile on the basis of an observation mode designated by the user.

Here, the observation mode includes, for example, a visible light/infrared light time-division imaging mode and an assist mode. The visible light/infrared light time-division imaging mode is a mode in which light emission of visible light by the external light source 30 and light emission of infrared light by the light source unit 202 are alternately performed, and imaging is sequentially performed by the image pickup unit 200 frame by frame at the respective light emission timings. Here, the visible light is an example of first light in the present disclosure, and the infrared light is an example of second light in the present disclosure. Further, the assist mode is a mode in which the light source unit 202 is caused to emit visible light so as to compensate for a lack of a light amount of the external light source 30. For example, the assist mode is a mode in which the light emission amount of visible light by the light source unit 202 is sequentially adjusted so that a sum of the light emission amount of the external light source 30 and the light emission amount of the light source unit 202 becomes substantially constant. Note that, in the assist mode, the light source unit 202 may be further controlled to emit visible light of illumination color which is substantially the same as that of the external light source 30.

Figure 4:
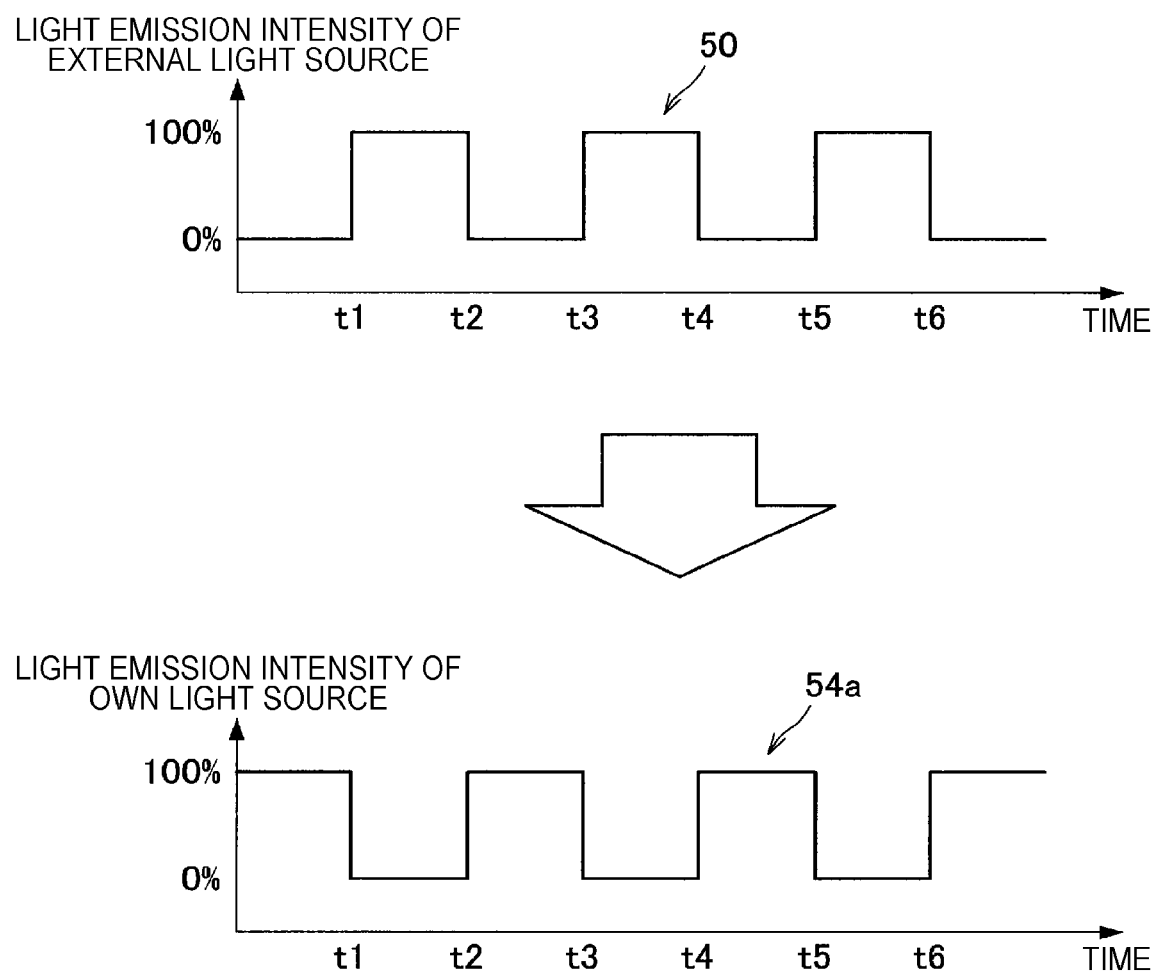
FIG. 4 is an explanatory diagram illustrating a generation example of own light source profile according to the first embodiment.

FIG. 4 is an explanatory diagram illustrating a generation example of the own light source profile in the case where the visible light/infrared light time-division imaging mode is designated as the observation mode. In this case, as illustrated in a waveform 54a (of the light emission intensity of the light source unit 202) in FIG. 4, the own light source profile generating unit 102 generates the own light source profile for controlling the light source unit 202 to emit infrared light at light emission intensity of, for example, 100% during a period in which the external light source 30 does not emit light (such as between time t2 and time t3) and controlling the light source unit 202 not to emit light during a period in which the external light source 30 emits light (such as between time t3 and time t4).

Figure 5:
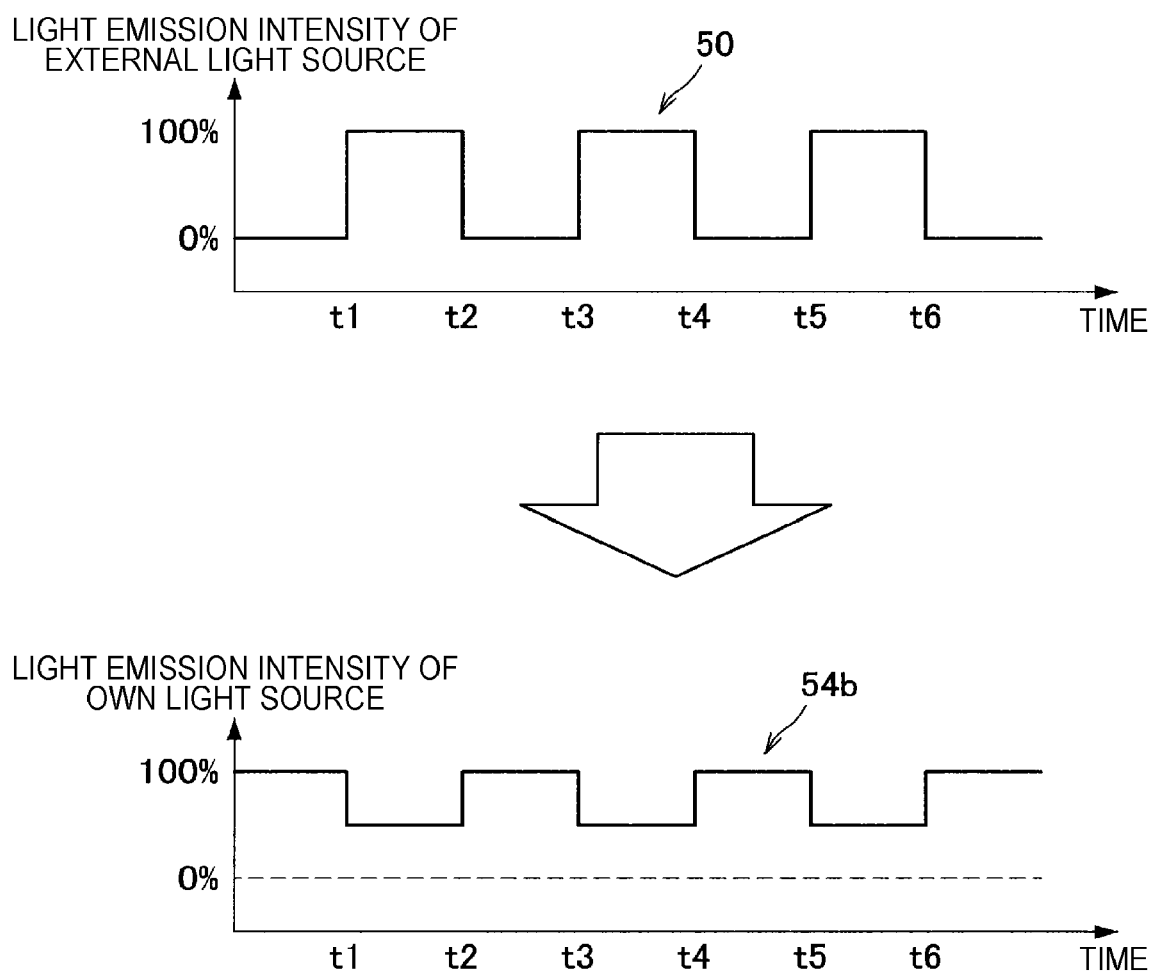
FIG. 5 is an explanatory diagram illustrating another generation example of the own light source profile according to the first embodiment.

Further, FIG. 5 is an explanatory diagram illustrating a generation example of the own light source profile in the case where the assist mode is designated as the observation mode. In this case, as illustrated in a waveform 54b (of light emission intensity of the light source unit 202) in FIG. 5, the own light source profile generating unit 102 generates the own light source profile for controlling the light source unit 202 to emit visible light at light emission intensity of "100%" during a period in which the external light source 30 does not emit light (such as between time t2 and time t3), and controlling the light source unit 202 to emit visible light at predetermined light emission intensity lower than "100%" during a period in which the external light source 30 emits light (such as between time t3 and time t4). Here, the predetermined light emission intensity can be light emission intensity of the light source unit 202 which is equal to a difference between the light emission intensity of "100%" of the light source unit 202 and the light emission intensity of "100%" of the external light source 30.

Note that setting information of the observation mode can be stored within the control apparatus 10-1. Further, the observation mode can be changed as needed on the basis of user operation with respect to, for example, an operation unit (not illustrated). This operation unit may be an operation unit of the above-described observation apparatus 20 or may be provided at the control apparatus 10-1 or may be separately provided within the surgery room.

Further, the own light source profile generating unit 102 transmits the generated own light source profile to the light source control unit 108.

{1-2-3. Synchronization Signal Analyzing Unit 104}

The synchronization signal analyzing unit 104 is an example of a synchronization signal specifying unit in the present disclosure. The synchronization signal analyzing unit 104 analyzes the synchronization signal in real time by analyzing a cycle and a timing to be synchronized on the basis of the image picked up by the image pickup unit 200. For example, in the example illustrated in FIG. 3, the synchronization signal analyzing unit 104 analyzes the synchronization signal 52 as illustrated in a graph (b) in FIG. 3 on the basis of a timing at which brightness of an image 40 picked up by the image pickup unit 200 changes. As an example, the synchronization signal analyzing unit 104 analyzes a timing at which the external light source 30 starts light emission from a state where the external light source 30 does not emit light, as an output timing of the synchronization signal.

Further, the synchronization signal analyzing unit 104 transmits the analyzed synchronization signal to the synchronization control unit 106.

{1-2-4. Synchronization Control Unit 106}

The synchronization control unit 106 is an example of an imaging control unit in the present disclosure. The synchronization control unit 106 generates a synchronization signal for the image pickup unit and a synchronization signal for the own light source on the basis of the synchronization signal analyzed by the synchronization signal analyzing unit 104. For example, the synchronization control unit 106 generates the synchronization signal for the image pickup unit and the synchronization signal for the own light source by adjusting a synchronization frequency and a synchronization phase on the basis of the synchronization signal analyzed by the synchronization signal analyzing unit 104. Further, the synchronization control unit 106 transmits the generated synchronization signal for the own light source to the light source control unit 108.

Further, the synchronization control unit 106 can control imaging on the image pickup unit 200 on the basis of the generated synchronization signal for the image pickup unit. For example, the synchronization control unit 106 controls the image pickup unit 200 to start imaging of a new frame in synchronization with the output timing of the synchronization signal for the image pickup unit. Alternatively, the synchronization control unit 106 can also provide the generated synchronization signal for the image pickup unit (itself) to the image pickup unit 200. In this case, the image pickup unit 200 performs imaging on the basis of the received synchronization signal for the image pickup unit.

FIG. 6 is a diagram illustrating a graph (a) illustrating a waveform of light emission intensity of the external light source 30, a graph (b) illustrating temporal change of light emission control on the light source unit 202, and a graph (c) illustrating temporal change of imaging control on the image pickup unit 200. Note that FIG. 6 illustrates a case where the visible light/infrared light time-division imaging mode is designated as the observation mode. As illustrated in FIG. 6, the synchronization control unit 106 controls the image pickup unit 200 so as to start imaging of a new frame at each timing at which a light emission state of the external light source 30 is switched between ON and OFF. By this means, imaging is performed frame by frame in the light emission period of the visible light by the external light source 30 and a light emission period of the infrared light by the light source unit 202 every time the external light source 30 blinks. Then, it is possible to display a sharp image in which a frame image 560 picked up upon light emission by the external light source 30 is superimposed on a frame image 562 picked up upon light emission of the infrared light immediately after the frame image 560, at the display apparatus 32.

{1-2-5. Light Source Control Unit 108}

The light source control unit 108 controls light emission of the light source unit 202 on the basis of the own light source profile generated by the own light source profile generating unit 102 and the synchronization signal for the own light source generated by the synchronization control unit 106. In the example illustrated in FIG. 6, the light source control unit 108 controls light emission of the light source unit 202 so that a light emission state of the light source unit 202 is switched from OFF to ON at a timing (for example, time t2) at which a light emission state of the external light source 30 is switched from ON to OFF. Note that, as described above, because the light source unit 202 can be a semiconductor light source, it is possible radiate light with a good response to control by the light source control unit 108.

Note that the configuration of the control apparatus 10-1 according to the first embodiment is not limited to the above-described example. For example, one or more of the external light source profile analyzing unit 100, the own light source profile generating unit 102, the synchronization signal analyzing unit 104, the synchronization control unit 106 and the light source control unit 108 may be provided within the observation apparatus 20 instead of being provided within the control apparatus 10-1.

<1-3. Operation>

Figure 7:
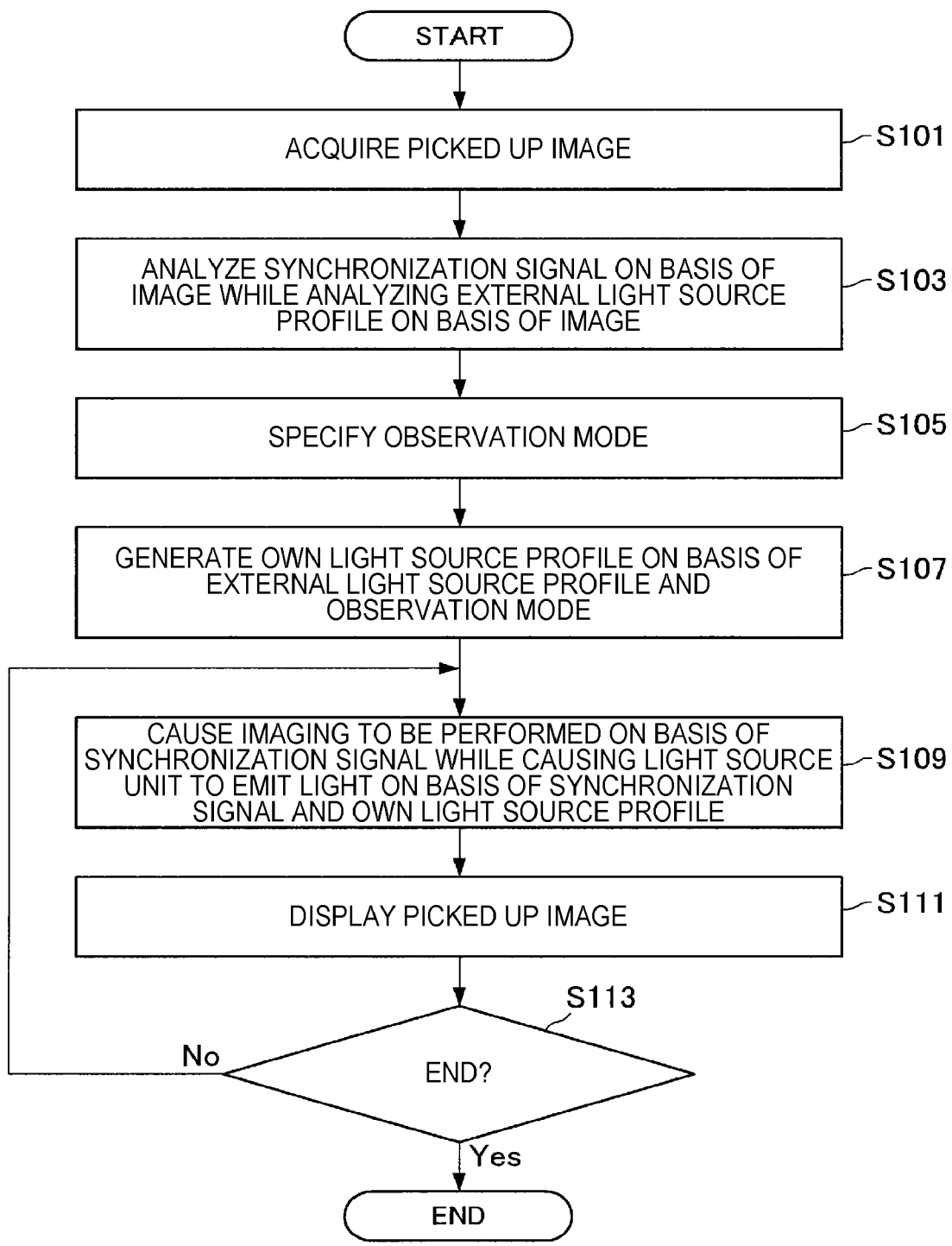
FIG. 7 is a flowchart illustrating an operation example according to the first embodiment.

The configuration according to the first embodiment has been described above. Operation according to the first embodiment will be described next with reference to FIG. 7. FIG. 7 is a flowchart illustrating an operation example according to the first embodiment.

As illustrated in FIG. 7, first, the control apparatus 10-1 acquires an image of a subject which is irradiated with light from the external light source 30, which is picked up by the image pickup unit 200, from the image pickup unit 200 (S101).

Subsequently, the external light source profile analyzing unit 100 analyzes the external light source profile on the basis of the acquired image. At the same time, the synchronization signal analyzing unit 104 analyzes the synchronization signal on the basis of the acquired image (S103).

Subsequently, the own light source profile generating unit 102 specifies the observation mode designated by the user, which is stored within, for example, the control apparatus 10-1 (S105). The own light source profile generating unit 102 then generates the own light source profile on the basis of the external light source profile analyzed in S103 and the observation mode specified in S105 (S107).

Subsequently, the synchronization control unit 106 generates the synchronization signal for the image pickup unit and the synchronization signal for the own light source on the basis of the synchronization signal analyzed in S103. The light source control unit 108 then causes the light source unit 202 to emit light on the basis of the generated synchronization signal for the own light source and the own light source profile generated in S107. At the same time, the synchronization control unit 106 causes the image pickup unit 200 to perform imaging on the basis of the generated synchronization signal for the image pickup unit (S109).

Then, the control apparatus 10-1 causes the display apparatus 32 to display the image picked up in S109 (S111). Then, in the case where observation end operation is performed by the user (S113: Yes), the present operation is finished. Meanwhile, in the case where observation end operation is not performed (S113: No), the control apparatus 10-1 repeats the process in S109 and subsequent processes again.

<1-4. Effects>

As described above, according to the first embodiment, the control apparatus 10-1 controls light emission of the light source unit 202 on the basis of the external light source profile specified on the basis of a picked up image of a subject irradiated with light emitted from the external light source 30 and the synchronization signal specified on the basis of the picked up image. By this means, it is possible to cause the light source unit 202 to adaptively emit light at a timing at which brightness of the light emitted from the external light source 30 changes.

For example, in the case where the visible light/infrared light time-division imaging mode is designated by the user as the observation mode, the control apparatus 10-1 causes the light source unit 202 to emit infrared light only during a period in which the external light source 30 does not emit light. Therefore, during open procedure, it is possible to perform visible light observation and infrared excitation fluorescent observation using the ICG without turning off the external light source 30 (that is, without darkening inside of the surgery room), so that it is possible to improve convenience during surgery.

Further, in the case where the assist mode is designated by the user as the observation mode, the control apparatus 10-1 sequentially adjusts a light emission amount of the visible light by the light source unit 202 so that a sum of the light emission amount by the external light source 30 and the light emission amount by the light source unit 202 becomes substantially constant. By this means, it is possible to prevent occurrence of artifact due to the external light source 30, such as, for example, banding and flicker in the image picked up by the image pickup unit 200. Further, it is possible to compensate for a lack of a light amount of the external light source 30. Therefore, it is possible to pick up a sharper image of a surgical region and display the image at the display apparatus 32, so that it is possible to perform surgery more safely and more reliably.

<1-5. Application Example>

The first embodiment has been described above. As described above, the control apparatus 10-1 causes the image pickup unit 200 to perform imaging at a frequency in accordance with the light emission frequency of the external light source 30. Therefore, in the case where the external light source 30 blinks at an extremely high frequency such as 1000 Hz, a length of an exposure period per frame becomes extremely short. Accordingly, a sufficient exposure amount cannot be obtained for individual frames, and a dark image can be picked up.

Figure 8:
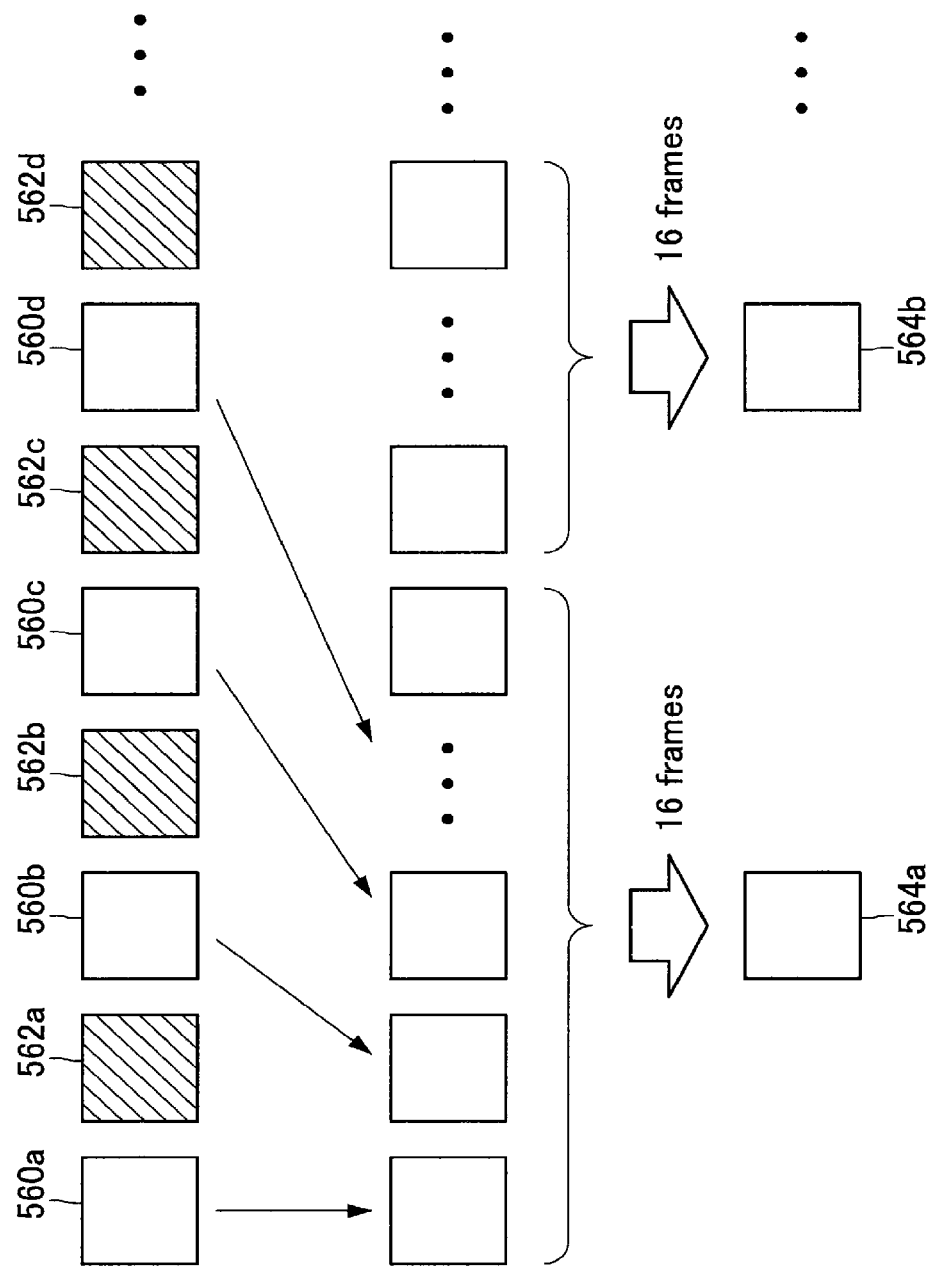
FIG. 8 is an explanatory diagram illustrating a generation example of an image for display according to an application example of the first embodiment.

Therefore, as an application example of the first embodiment, the control apparatus 10-1 can also generate an image for display on the basis of frame images of the number in accordance with the light emission frequency of the external light source 30, which are picked up by the image pickup unit 200. Here, the above-described functions will be described in more detail with reference to FIG. 8. FIG. 8 is an explanatory diagram illustrating a generation example of the image for display (image for display 564) in the visible light/infrared light time-division imaging mode. Note that, while FIG. 8 illustrates a generation example of the image for display 564 regarding the frame image 560 picked up during light emission of the visible light (that is, while the external light source 30 emits light), the image for display regarding the frame image 562 picked up during light emission of the infrared light by the light source unit 202 is also generated with a similar method.

As illustrated in FIG. 8, the control apparatus 10-1 generates the image for display 564 by performing an addition process for each of the frame images 560 of the number (16 in the example illustrated in FIG. 8) in accordance with the light emission frequency of the external light source 30, which are picked up by the image pickup unit 200, on the frame images 560 of the corresponding number. For example, the control apparatus 10-1 generates the image for display 564 by adding pixel values of pixels within the plurality of frame images 560 for each pixel. By this means, even in the case where the external light source 30 blinks at a high frequency, because it becomes possible to display a bright image, this example is effective particularly in the visible light/infrared light time-division imaging mode.

2. Second Embodiment

The first embodiment has been described above. As described above, in the first embodiment, the control apparatus 10-1 specifies the external light source profile on the basis of the picked up image of the subject which is irradiated with the light emitted from the external light source 30.

A second embodiment will be described next. As will be described later, the control apparatus 10-2 according to the second embodiment can specify the external light source profile on the basis of a measurement result of the light emitted from the external light source 30.

<2-1. Configuration of Control System>

Figure 9:
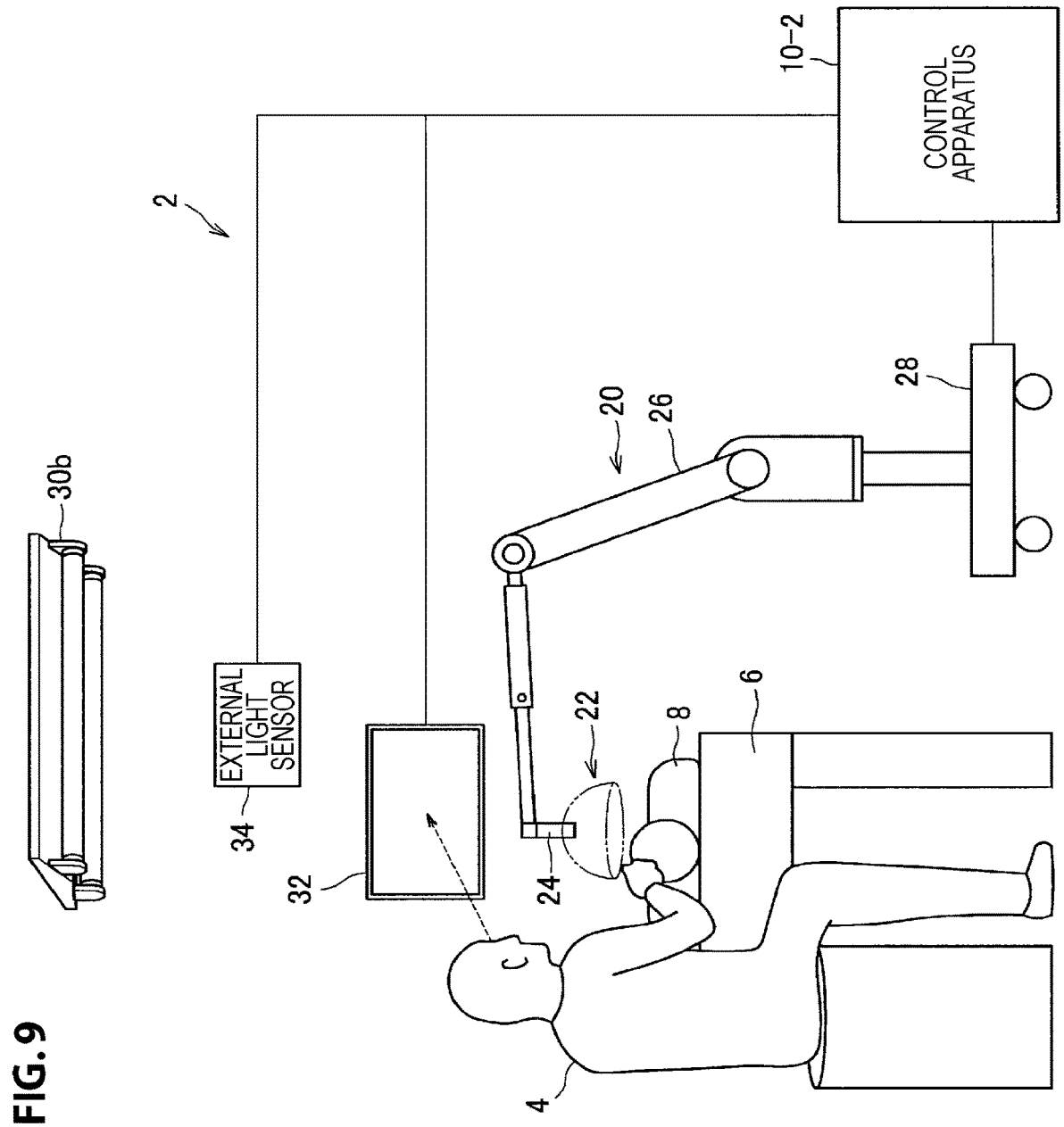
FIG. 9 is an explanatory diagram illustrating a configuration example of a control system according to a second embodiment.

FIG. 9 is an explanatory diagram illustrating a configuration example of a control system according to the second embodiment. As illustrated in FIG. 9, the control system according to the second embodiment further includes an external light sensor 34 compared to the first embodiment and includes a control apparatus 10-2 in place of the control apparatus 10-1. Further, as illustrated in FIG. 9, in the second embodiment, it is assumed that the external light source 30 is a light source of a type whose waveform of light emission intensity does not become a rectangular wave, such as, for example, fluorescent lighting 30b. Note that, in the following description, only features different from those in the first embodiment will be described, and description of overlapped features will be omitted.

{2-1-1. External Light Sensor 34}

The external light sensor 34 is a sensor which detects energy of ambient light. The external light sensor 34 can be a photoconductive or photoelectromotive force sensor. For example, the external light sensor 34 measures an amount of the light emitted from the external light source 30. Further, the external light sensor 34 can perform communication with the control apparatus 10-2 through wired or wireless communication.

<2-2. Configuration>

Figure 10:
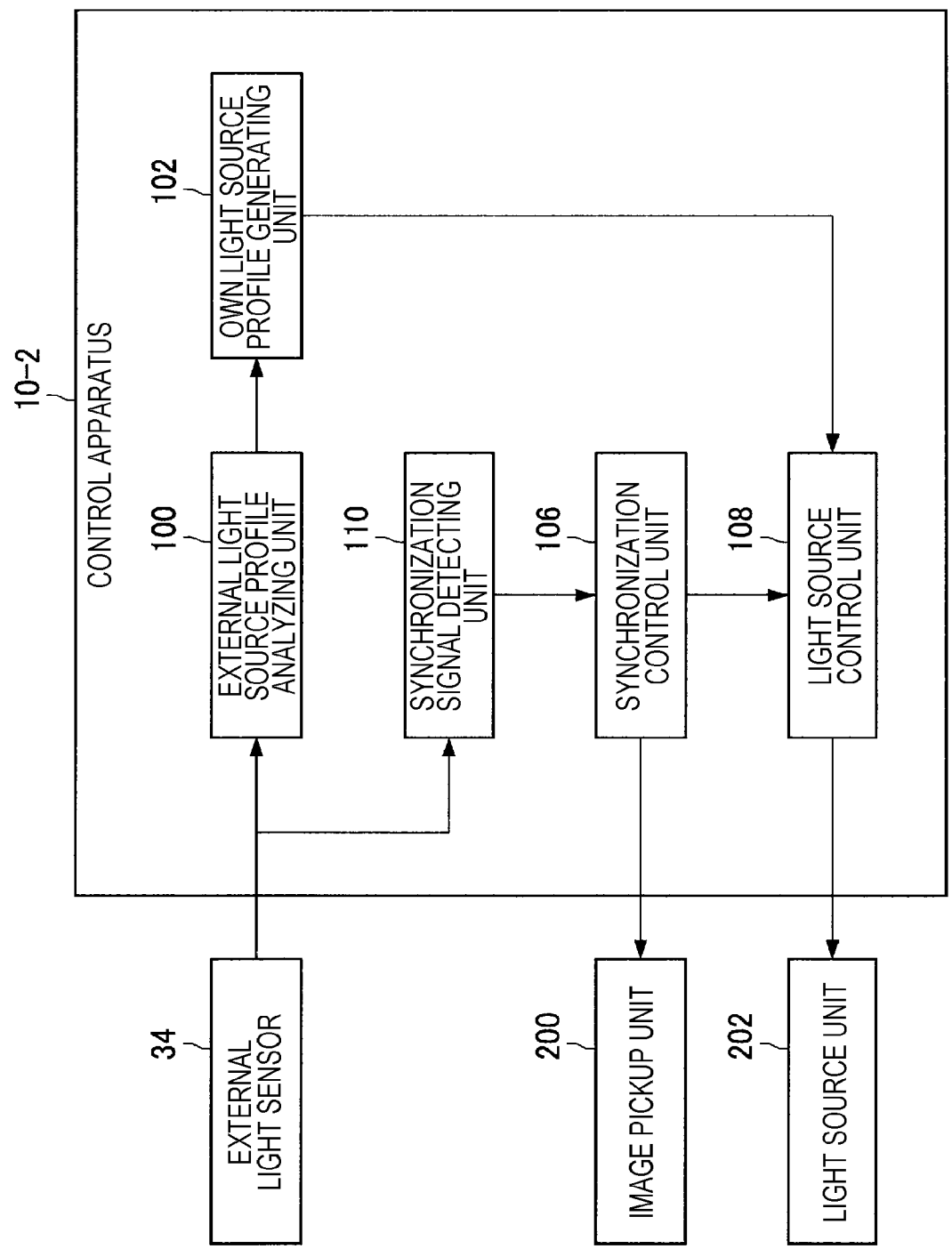
FIG. 10 is a functional block diagram illustrating a configuration example of a control apparatus 10-2 according to the second embodiment.

A configuration of the control apparatus 10-2 according to the second embodiment will be described in detail next. FIG. 10 is a functional block diagram illustrating a configuration example of the control apparatus 10-2 according to the second embodiment. As illustrated in FIG. 10, the control apparatus 10-2 further includes a synchronization signal detecting unit 110 and does not include the synchronization signal analyzing unit 104 compared to the control apparatus 10-1 illustrated in FIG. 2. Note that, in the following description, only components having functions different from those in the first embodiment will be described.

{2-2-1. External Light Source Profile Analyzing Unit 100}

The external light source profile analyzing unit 100 according to the second embodiment analyzes the external light source profile on the basis of a measurement result of the light emitted from the external light source 30 by the external light sensor 34. For example, the external light source profile analyzing unit 100 analyzes the external light source profile on the basis of time series of the measurement result of the light emission amount from the external light source 30.

{2-2-2. Own Light Source Profile Generating Unit 102}

The own light source profile generating unit 102 according to the second embodiment generates the own light source profile on the basis of comparison between the external light source profile analyzed by the external light source profile analyzing unit 100 and a target light amount set in advance. Note that the target light amount can be stored within the control apparatus 10-2. Further, the target light amount can be changed as needed on the basis of, for example, user operation with respect to an operation unit.

FIG. 11 is an explanatory diagram illustrating a generation example of the own light source profile according to the second embodiment. Note that the waveform 50 (of the light emission amount of the external light source 30) illustrated in FIG. 11 indicates an example of temporal change of the light emission amount corresponding to the analyzed external light source profile. As illustrated in a region 54 in FIG. 11, the own light source profile generating unit 102 generates the own light source profile for sequentially adjusting a light emission amount of visible light by the light source unit 202 so as to be equal to a difference between the target light amount and the light emission amount of the external light source 30.

{2-2-3. Synchronization Signal Detecting Unit 110

The synchronization signal detecting unit 110 is an example of a synchronization signal specifying unit in the present disclosure. The synchronization signal detecting unit 110 detects a synchronization signal by specifying a cycle and a timing to be synchronized on the basis of a measurement result of the light emitted from the external light source 30 by the external light sensor 34. For example, as illustrated in FIG. 12, the synchronization signal detecting unit 110 detects a timing at which the light emission amount from the external light source 30 changes from decrease to increase (such as, for example, time t2 and time t3) as an output timing of the synchronization signal. Further, the synchronization signal detecting unit 110 transmits the detected synchronization signal to the synchronization control unit 106.

{2-2-4. Synchronization Control Unit 106}

The synchronization control unit 106 according to the second embodiment transmits the synchronization signal detected by the synchronization signal detecting unit 110 to the light source control unit 108.

Note that, in the second embodiment, as described above, because a sum of the light emission amount by the external light source 30 and the light emission amount by the light source unit 202 becomes substantially constant, even if light emission by the light source unit 202 is not in synchronization with imaging by the image pickup unit 200, it is possible to substantially suppress occurrence of artifact. However, to further improve image quality, it is desirable that the synchronization control unit 106 causes the image pickup unit 200 to perform imaging on the basis of the synchronization signal detected by the synchronization signal detecting unit 110. By this means, it is possible to make a ratio between the light emission amount by the external light source 30 and the light emission amount by the light source unit 202 substantially constant for each frame, so that it is possible to stabilize color shade for each frame.

<2-3. Operation>

Figure 13:
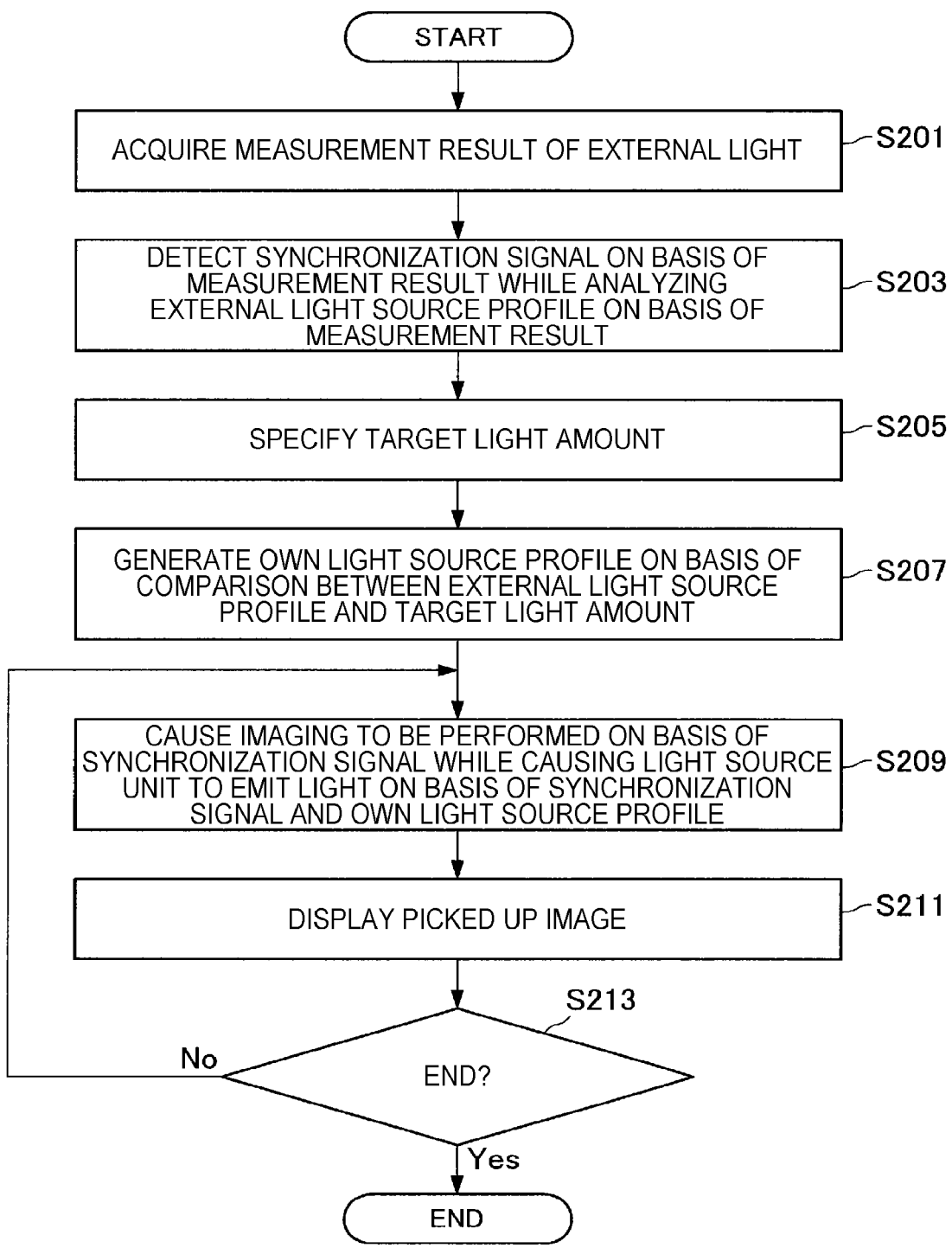
FIG. 13 is a flowchart illustrating an operation example according to the second embodiment.

The configuration according to the second embodiment has been described above. Operation according to the second embodiment will be described next with reference to FIG. 13. FIG. 13 is a flowchart illustrating the operation example according to the second embodiment.

As illustrated in FIG. 13, first, the control apparatus 10-2 acquires the measurement result of the light emitted from the external light source 30 by the external light sensor 34 from the external light sensor 34 (S201).

Subsequently, the external light source profile analyzing unit 100 analyzes the external light source profile on the basis of the acquired measurement result. At the same time, the synchronization signal detecting unit 110 detects a synchronization signal on the basis of the acquired measurement result (S203).

Subsequently, the own light source profile generating unit 102 specifies the set target light amount stored within, for example, the control apparatus 10-1 (S205). The own light source profile generating unit 102 then generates the own light source profile on the basis of comparison between the external light source profile analyzed in S203 and the target light amount specified in S205 (S207).

Subsequently, the light source control unit 108 controls light emission of the light source unit 202 on the basis of the synchronization signal detected in S203 and the own light source profile generated in S207. At the same time, the synchronization control unit 106 controls imaging of the image pickup unit 200 on the basis of the synchronization signal detected in S203 (S209).

Note that the processes from S211 to S213 illustrated in FIG. 13 are similar to processes from S111 to S113 according to the first embodiment.

<2-4. Effects>

As described above, according to the second embodiment, the control apparatus 10-2 specifies the external light source profile and the synchronization signal on the basis of the measurement result of the light emitted from the external light source 30, and, then, controls light emission of the light source unit 202 on the basis of comparison between the external light source profile and the target light amount, and the synchronization signal. By this means, for example, it is possible to cause the light source unit 202 to emit light so that a sum of the light emission amount by the external light source 30 and the light emission amount by the light source unit 202 becomes substantially constant. Therefore, it is possible to prevent occurrence of artifact due to the external light source 30 in the image picked up by the image pickup unit 200.

2. Third Embodiment

The second embodiment has been described above. As described above, in the first embodiment and the second embodiment, a scene is assumed where the control apparatus 10 cannot control the external light source 30.

A third embodiment will be described next. In the third embodiment, a scene is assumed where the control apparatus 10 can control light emission of the external light source 30.

As will be described later, a control apparatus 10-3 according to the third embodiment can control light emission of the light source unit 202 and the external light source 30 on the basis of the synchronization signal specified on the basis of the light emitted from the external light source 30.

<3-1. Configuration>

{3-1-1. Control Apparatus 10-3}

Figure 14:
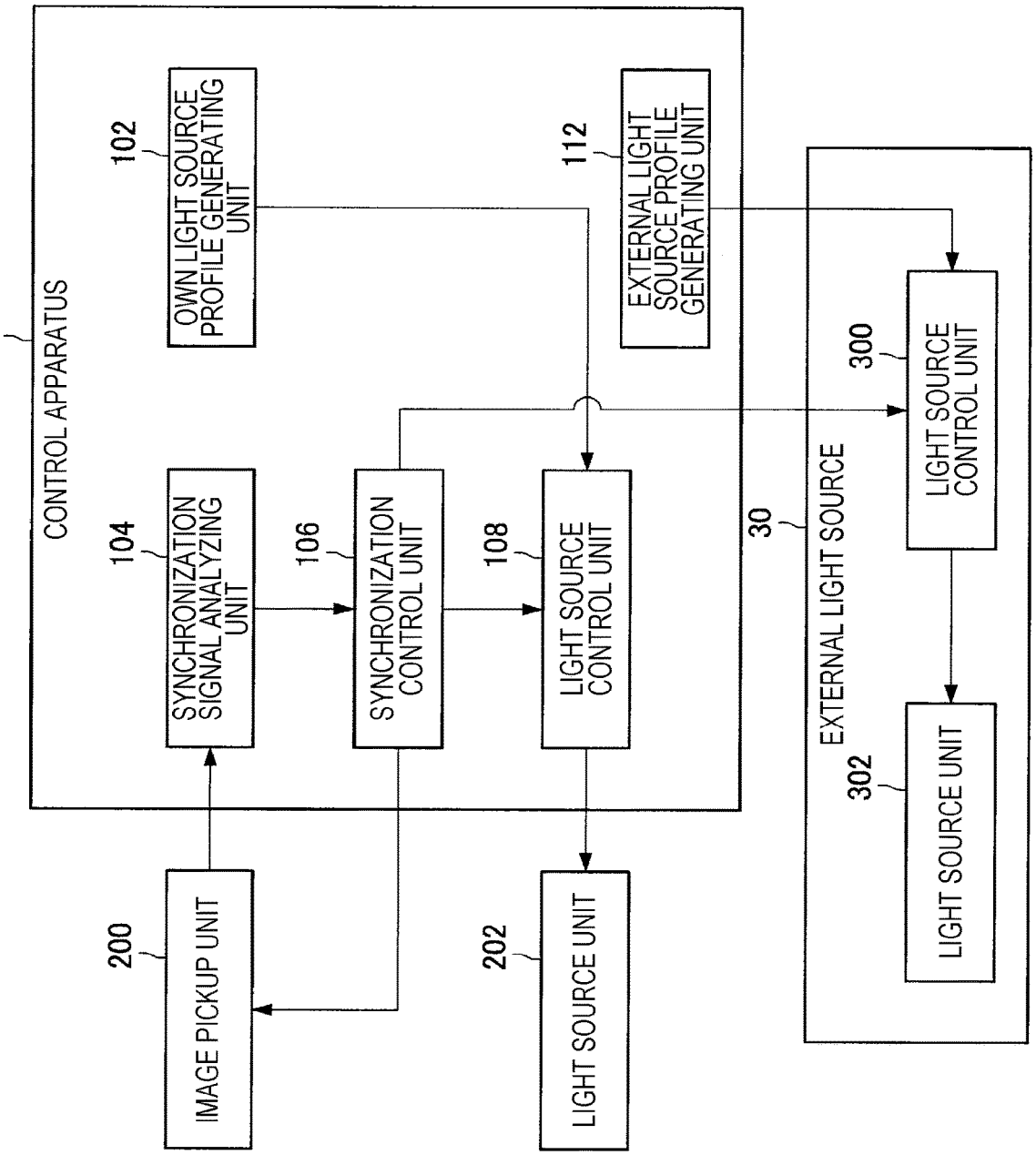
FIG. 14 is a functional block diagram illustrating a configuration example of a control apparatus 10-3 according to a third embodiment.

First, a configuration according to the third embodiment will be described in detail. FIG. 14 is a functional block diagram illustrating a configuration example of the control apparatus 10-3 and the external light source 30 according to the third embodiment. As illustrated in FIG. 14, the control apparatus 10-3 further includes an external light source profile generating unit 112 and does not include the external light source profile analyzing unit 100 compared to the control apparatus 10-1 illustrated in FIG. 2. Note that, in the following description, only components having functions different from those in the first embodiment will be described.

(3-1-1-1. External Light Source Profile Generating Unit 112)

The external light source profile generating unit 112 generates the external light source profile on the basis of predetermined information. Here, the predetermined information may include setting information regarding cooperation operation between the external light source 30 and the light source unit 202 or may include information of specifications of the external light source 30. Further, the external light source profile generating unit 112 provides the generated external light source profile to the external light source 30.

(3-1-1-2. Own Light Source Profile Generating Unit 102)

The own light source profile generating unit 102 according to the third embodiment generates the own light source profile on the basis of the observation mode designated by the user. For example, the own light source profile generating unit 102 generates the own light source profile such that the light emission frequency is the same as the light emission frequency in the external light source profile generated by the external light source profile generating unit 112 and a phase difference is an angle (such as, for example, 180 degrees and 0 degree) in accordance with the designated observation mode.

(3-1-1-3. Synchronization Control Unit 106)

The synchronization control unit 106 according to the third embodiment further generates the synchronization signal for the external light source on the basis of the synchronization signal analyzed by the synchronization signal analyzing unit 104 and, then, provides the generated synchronization signal for the external light source to the external light source 30. Alternatively, the synchronization control unit 106 may provide the synchronization signal itself analyzed by the synchronization signal analyzing unit 104 to the external light source 30.

{3-1-2. External Light Source 30}

As illustrated in FIG. 14, the external light source 30 includes a light source control unit 300 and a light source unit 302.

(3-1-2-1. Light Source Control Unit 300)

The light source control unit 300 is an example of a light source control unit in the present disclosure. The light source control unit 300 controls light emission of the light source unit 302 on the basis of the external light source profile provided from the control apparatus 10-3 and the synchronization signal for the external light source (or the synchronization signal) provided from the control apparatus 10-3.

(3-1-2-2. Light Source Unit 302)

The light source unit 302 can be a semiconductor light source such as an LED, fluorescent lighting, or the like. The light source unit 302 emits light in accordance with control by the light source control unit 300.

<3-2. Effects>

As described above, according to the third embodiment, the control apparatus 10-3 controls light emission of the light source unit 202 and the external light source 30 on the basis of the synchronization signal specified on the basis of the light emitted from the external light source 30 and the observation mode designated by the user. In this manner, by causing the external light source 30 and the light source unit 202 to operate in cooperation with each other, it is possible to emit light further appropriate for the observation mode designated by the user. As a result, it is possible to further improve image quality of the picked up image.

4. Modified Examples

The preferred embodiment of the present disclosure has been described above with reference to the accompanying drawings, whilst the present disclosure is not limited to the above examples. A person skilled in the art may find various alterations and modifications within the scope of the appended claims, and it should be understood that they will naturally come under the technical scope of the present disclosure.

For example, while, in FIG. 1 and FIG. 9, only one (or one set of) external light source 30 is illustrated, the present disclosure is not limited to such an example, and one or more types of a plurality of external light sources 30 may be provided within the surgery room. In this case, the control apparatus 10-1 or the control apparatus 10-2 may specify the external light source profile and the synchronization signal on the basis of the picked up image of the subject irradiated with light emitted from all the external light sources 30 or the measurement result by the external light sensor 34. The control apparatus 10 may then control light emission of the light source unit 202 on the basis of the specified external light source profile and the specified synchronization signal.

Further, the respective steps in operation of the above-described embodiments do not have to be necessarily processed in the described order. For example, the respective steps may be processed in order which has been changed as appropriate. Further, the respective steps may be processed partially in parallel or individually instead of being processed in chronological order. Further, part of the described steps may be omitted or another step may be further added.

Further, according to the above-described respective embodiments, it is also possible to provide a computer program for causing hardware such as a processor such as a CPU and a GPU, a storage element such as a memory, and/or a programmable logic device such as an FPGA to exert functions equivalent to those of respective components of the control apparatus 10 according to the above-described respective embodiments. Further, a recording medium in which the computer program is recorded is also provided.

Further, the effects described in this specification are merely illustrative or exemplified effects, and are not limitative. That is, with or in the place of the above effects, the technology according to the present disclosure may achieve other effects that are clear to those skilled in the art from the description of this specification.

Additionally, the present technology may also be configured as below.

(1)

A control apparatus including:

a light source control unit configured to control light emission of a second light source on the basis of profile of light emitted from a first light source and a synchronization signal for synchronizing a timing between the first light source and the second light source for radiating light on a surgical region.

(2)

The control apparatus according to (1), in which the profile includes information regarding regularity of change of brightness of the light emitted from the first light source.

(3)

The control apparatus according to (2), in which the profile includes a modulation pattern of the light emitted from the first light source, a light emission frequency or illumination color of the light.

(4)

The control apparatus according to (2) or (3), further including:

a profile specifying unit configured to specify the profile by analyzing a picked up image of a subject irradiated with the light emitted from the first light source.

(5)

The control apparatus according to (2) or (3), further including:

a profile specifying unit configured to specify the profile by analyzing a measurement result of the light emitted from the first light source.

(6)

The control apparatus according to any one of (2) to (5), in which the light source control unit changes light emission intensity of the second light source in accordance with change of intensity of the light emitted from the first light source, the intensity being indicated in the profile.

(7)

The control apparatus according to (6), in which the light source control unit causes the second light source to emit light during a period in which light is not emitted from the first light source and does not cause the second light source to emit light during a period in which light is emitted from the first light source.

(8)

The control apparatus according to (7), in which the first light source emits first light, and the second light source emits second light of a type different from a type of the first light.

(9)

The control apparatus according to (6), in which the light source control unit controls light emission of the second light source so that light emission intensity of the second light source becomes higher as the intensity of the light emitted from the first light source becomes lower.

(10)

The control apparatus according to (6) or (9), in which the light source control unit determines a light emission amount of the second light source on the basis of comparison between a light amount of the light emitted from the first light source and a target light amount.

(11)

The control apparatus according to (9) or (10), in which the first light source and the second light source emit a same type of light.

(12)

The control apparatus according to any one of (6) to (11), in which the light source control unit further controls light emission of the second light source on the basis of an observation mode designated by a user.

(13)

The control apparatus according to any one of (2) to (12), further including:

a synchronization signal specifying unit configured to specify the synchronization signal by analyzing a picked up image of a subject irradiated with the light emitted from the first light source.

(14)

The control apparatus according to any one of (2) to (12), further including:

a synchronization signal specifying unit configured to specify the synchronization signal on the basis of a measurement result of the light emitted from the first light source.

(15)

The control apparatus according to any one of (1) to (14), further including:

an imaging control unit configured to control imaging of an image pickup unit on the basis of the synchronization signal.

(16)

The control apparatus according to (15), in which the imaging control unit causes the image pickup unit to perform imaging in synchronization with the synchronization signal.

(17)

The control apparatus according to any one of (1) to (16), in which the light source control unit further controls light emission of the first light source on the basis of the profile and the synchronization signal.

(18)

The control apparatus according to any one of (1) to (17), in which the second light source is a semiconductor light source.

(19)

A control system including:

a first light source;

a second light source configured to radiate light on a surgical region;

an image pickup unit;

a light source control unit configured to control light emission of the second light source on the basis of profile of light emitted from the first light source, and a synchronization signal for synchronizing a timing between the first light source and the second light source; and an imaging control unit configured to control imaging of the image pickup unit on the basis of the synchronization signal.

(20)

A control method including:

controlling, by a processor, light emission of a second light source on the basis of profile of light emitted from a first light source and a synchronization signal for synchronizing a timing between the first light source and the second light source for radiating light on a surgical region.

REFERENCE SIGNS LIST 10-1, 10-2. 10-3 control apparatus
20 observation apparatus
22 observing unit
24 cylindrical portion
26 arm unit
28 base unit
30 external light source
32 display apparatus
34 external light sensor
100 external light source profile analyzing unit
102 own light source profile generating unit
104 synchronization signal analyzing unit
106 synchronization control unit
108, 300 light source control unit
110 synchronization signal detecting unit
112 external light source profile generating unit
200 image pickup unit
202, 302 light source unit

The invention claimed is:

1. A control apparatus comprising:

light source control circuitry configured to control light emission of a second light source on a basis of profile of light emitted from a first light source and a synchronization signal for synchronizing a timing between the first light source and the second light source for radiating light on a surgical region.

2. The control apparatus according to claim 1, wherein the profile includes information regarding regularity of change of brightness of the light emitted from the first light source.

3. The control apparatus according to claim 2, wherein the profile includes a modulation pattern of the light emitted from the first light source, a light emission frequency or illumination color of the light.

4. The control apparatus according to claim 2, further comprising:

profile specifying circuitry configured to specify the profile by analyzing a picked up image of a subject irradiated with the light emitted from the first light source.

5. The control apparatus according to claim 2, further comprising:

profile specifying circuitry configured to specify the profile by analyzing a measurement result of the light emitted from the first light source.

6. The control apparatus according to claim 2, wherein the light source control circuitry changes light emission intensity of the second light source in accordance with change of intensity of the light emitted from the first light source, the intensity being indicated in the profile.

7. The control apparatus according to claim 6, wherein the light source control circuitry causes the second light source to emit light during a period in which light is not emitted from the first light source and does not cause the second light source to emit light during a period in which light is emitted from the first light source.

8. The control apparatus according to claim 7, wherein the first light source emits first light, and
the second light source emits second light of a type different from a type of the first light.

9. The control apparatus according to claim 6, wherein the light source control circuitry controls light emission of the second light source so that light emission intensity of the second light source becomes higher as the intensity of the light emitted from the first light source becomes lower.

10. The control apparatus according to claim 6, wherein the light source control circuitry determines a light emission amount of the second light source on a basis of comparison between a light amount of the light emitted from the first light source and a target light amount.

11. The control apparatus according to claim 9, wherein the first light source and the second light source emit a same type of light.

12. The control apparatus according to claim 6, wherein the light source control circuitry further controls light emission of the second light source on a basis of an observation mode designated by a user.

13. The control apparatus according to claim 2, further comprising:
synchronization signal specifying circuitry configured to specify the synchronization signal by analyzing a picked up image of a subject irradiated with the light emitted from the first light source.

14. The control apparatus according to claim 2, further comprising:
synchronization signal specifying circuitry configured to specify the synchronization signal on a basis of a measurement result of the light emitted from the first light source.

15. The control apparatus according to claim 1, further comprising:
imaging control circuitry configured to control imaging of an image pickup sensor on a basis of the synchronization signal.

16. The control apparatus according to claim 15, wherein the imaging control circuitry causes the image pickup sensor to perform imaging in synchronization with the synchronization signal.

17. The control apparatus according to claim 1, wherein the light source control circuitry further controls light emission of the first light source on a basis of the profile and the synchronization signal.

18. The control apparatus according to claim 1, wherein the second light source is a semiconductor light source.

19. A control system comprising:
a first light source;
a second light source configured to radiate light on a surgical region;
an image pickup sensor;
light source control circuitry configured to control light emission of the second light source on a basis of profile of light emitted from the first light source, and a synchronization signal for synchronizing a timing between the first light source and the second light source; and
imaging control circuitry configured to control imaging of the image pickup sensor on a basis of the synchronization signal.

20. A control method comprising:
controlling, by a processor, light emission of a second light source on a basis of profile of light emitted from a first light source and a synchronization signal for synchronizing a timing between the first light source and the second light source for radiating light on a surgical region.

* * * * *